US00PP13682P29

(12) United States Plant Patent
Heims

(10) Patent No.: US PP13,682 P2
(45) Date of Patent: Mar. 25, 2003

(54) PULMONARIA PLANT NAMED 'BABY BLUE'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/080,060

(22) Filed: Feb. 19, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—Klarquist Sparkman LLP

(57) ABSTRACT

A new and distinct hybrid of Pulmonaria plant characterized by a compact habit and large, showy, medium blue colored flowers.

2 Drawing Sheets

BOTANICAL CLASSIFICATION

Pulmonaria hybrid.

VARIETY DENOMINATION

'Baby Blue'.

BACKGROUND OF THE INVENTION

The present invention relates to a new and distinct cultivar a hardy perennial of the genus Pulmonaria, and known by the cultivar name 'Baby Blue'. The genus Pulmonaria is a member of the family Boraginaceae.

The new cultivar originated as an open-pollinated cross between unknown parents in a field of selected hybrid Pulmonaria. This is known to be an outcross because Pulmonaria does not normally self-pollinate. Due to the fact that the instant plant and parent plants are interspecific hybrids from several generations of interbreeding and selecting, no species designations are given.

SUMMARY OF THE INVENTION

This new plant is characterized by:

1) Large, showy, medium blue colored flowers;

2) Leaves with short petioles and blades;

3) Heavy silvering on the summer leaves and spotting on the spring leaves;

4) Compact habit;

5) Excellent vigor and resistance to mildew.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
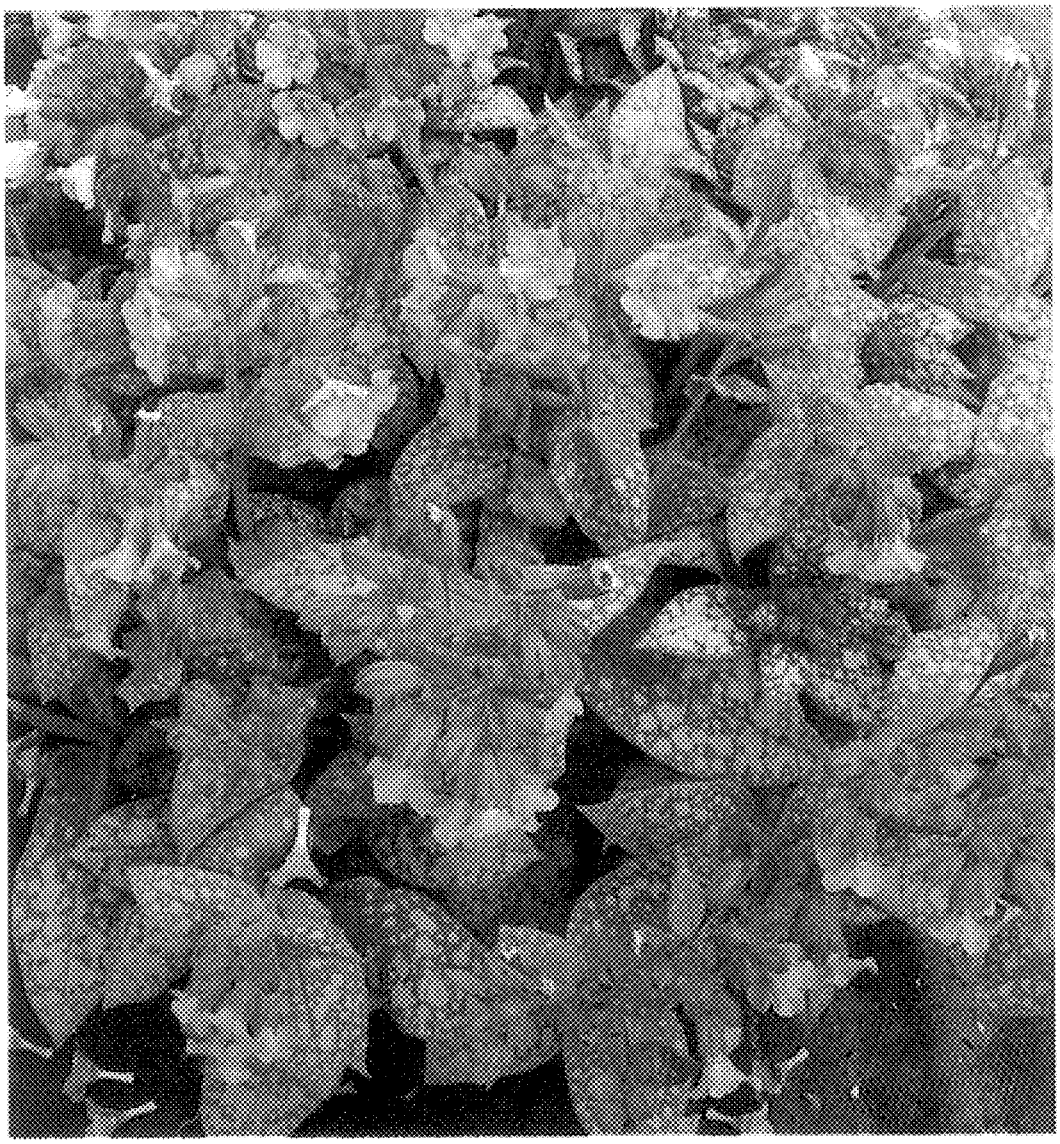
FIG. 1 shows Pulmonaria 'Baby Blue' in flower in the spring with spring foliage.
Figure 2:
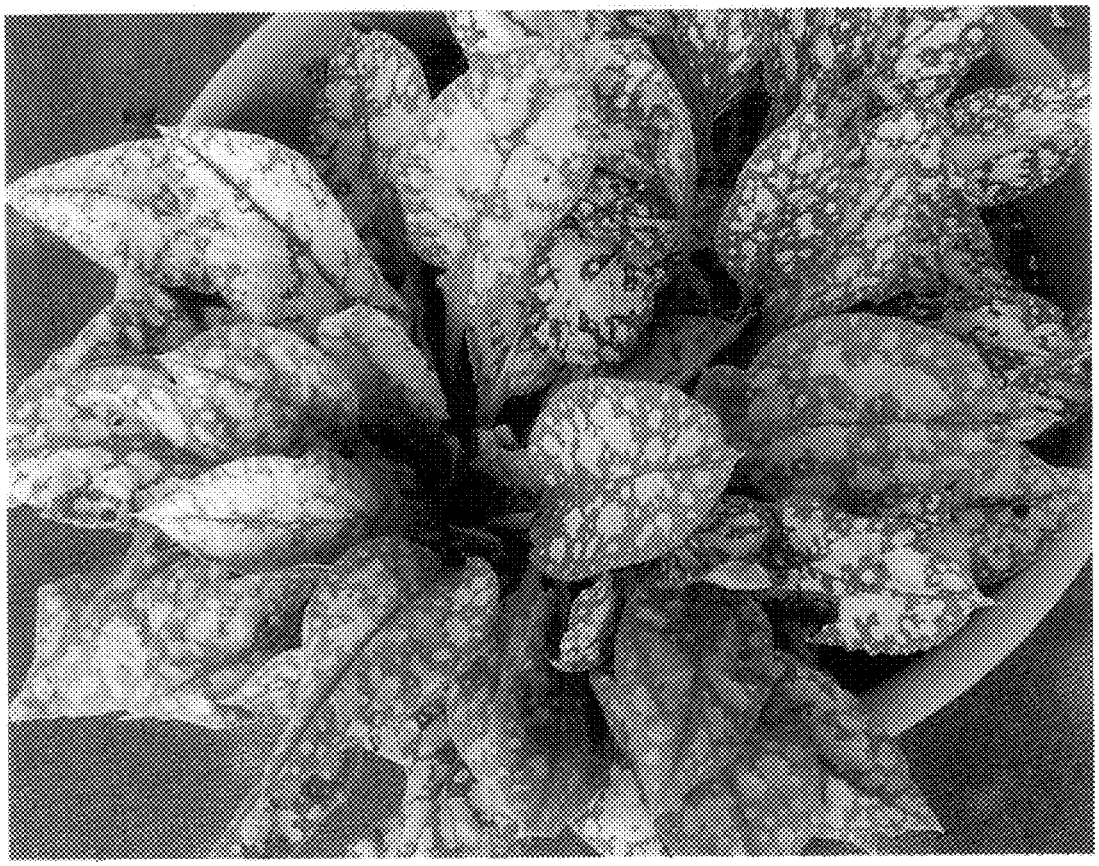
FIG. 2 shows the summer foliage.

The following is a detailed description of the new Pulmonaria hybrid based on observations of a three-year-old specimen grown in the ground in Canby, Oregon. The color descriptions are all based on The Royal Horticultural Society Colour Chart.

Botanical name: Pulmonaria hybrid.
Cultivar name: 'Baby Blue'.
Market class: Herbaceous perennial.
Plant:
- *Type.*—Herbaceous perennial.
- *Hardiness.*—USDA Zones 5 to 9.
- *Spring size.*—43 cm. wide and 20 cm. tall.
- *Summer size.*—43 cm. wide and 18 cm. tall.
- *Form.*—Basal clump.

Leaf:
- *Type.*—Simple.
- *Shape.*—Ovate to elliptic.
- *Arrangement.*—Rosette.
- *Blade length.*—12 to 14 cm.
- *Width.*—6.3 to 7.3 cm.
- *Margins.*—Entire and slightly undulate.
- *Apex.*—Acuminate.
- *Base.*—Attenuate.
- *Venation.*—Pinnate.
- *Texture.*—Scabrous.
- *Aspect.*—Matte.
- *Petiole size.*—4 to 8 cm long and 0.7 cm wide.
- *Petiole texture.*—Scabrous.
- *Petiole color.*—Yellow Green 146C.
- *Color.*—Topside: Green, Yellow Green 147A, with silver blotches, Greyed Green 194C. Bottom: Between Yellow Green 147B and C.

Cauline leaves (These are found only in the spring on the flowering stems. After the seed is produced these stems die out.):
- *Type.*—Simple.
- *Arrangement.*—Alternate.

*Shape.*—Variable. Ovate at the top to oblanceolate toward base.
*Length.*—8.5 cm.
*Width.*—3 to 3.5 cm.
*Margins.*—Entire, undulating slightly.
*Apex.*—Acuminate.
*Base.*—Clasping, sessile.
*Leaf texture.*—Scabrous.
*Venation.*—Pinnate.
*Color.*—Topside: Green, Yellow Green 146A, except where silver blotched or spotted, Greyed Green 193A. The silver spots or blotches are on the top ⅔ of the leaf. Bottom side: Between 147B and C.

Inflorescence:
*Type.*—Terminal forked cyme.
*Number of flowers per cyme.*—20.
*Peduncle.*—Height: 18 to 20 cm. Diameter: 0.5 cm. Vestiture: Scabrous and with glandular hairs. Color: Yellow Green 146C with Greyed Purple 183A in high sunlight.
*Pedicel.*—Length: Varies. 0.1 to 0.5 cm. Vestiture: Scabrous and with glandular hairs. Color: Greyed Purple 183A.

Flower bud:
*Size.*—1 cm. long and 0.6 cm. wide, with 0.5 cm of corolla exposed.
*Shape.*—Ovoid.
*Color.*—Rose pink, Red 48B.

Flower:
*Type.*—Actinomorphic.
*Shape.*—Rotate. (Very showy with lobes often at right angles to the tube.).
*Size.*—Large — 1.5 cm. deep and 2 cm. wide. Lobes 0.8 cm long.
*Corolla.*—5 fused petals with rounded, obtuse lobes.
*Color.*—Changes with age from rose pink, Red 48B in the newly opened flowers, to Violet 87C, to Violet Blue 97A in the fully open flowers.
*Calyx.*—5 fused sepals, campanulate, scabrous and glandular hairy.
*Calyx size.*—1.4 cm deep and 0.7 cm wide.
*Calyx color.*—Yellow Green 148B with Greyed Purple 183A on the sunny side.
*Pistil.*—Thrum in type, included in the corolla tube.
*Ovary position.*—Partly inferior.
*Carpel number.*—4.
*Stamen number.*—5, attached to and exerted from the tube.
*Pollen color.*—White 155C.
*Bloom period.*—Late February to late April in Canby, Oreg.
*Fragrance.*—None.

Seed:
*Type.*—4 smooth nutlets, usually Black 202A and shiny. Seeds not found to date.
*Fertility.*—Very low.

Disease: None observed on plant grown under commercial conditions in Canby, Oreg.

COMPARISONS TO SIMILAR PULMONARIA

Compared to Pulmonaria 'May Bouquet', (U.S. Plant Pat. No. 12,333), Pulmonaria 'Baby Blue' has a smaller habit, a lighter flower color, and lighter, broader, smaller leaves. They are similar in that they both have large flowers with a high flower count and short flowering stems.

Compared to Pulmonaria 'Dark Vader' (U.S. Plant. Pat. No. 12,336), this new cultivar has much larger flowers that are rotate rather than funnelform, lighter flower color, and smaller, more silvered leaves.

I claim:

1. A new and distinct hybrid of Pulmonaria plant substantially as shown and described, characterized by a compact habit and large, showy, medium blue colored flowers.

* * * * *